US012716827B2

(12) United States Patent
Gombrich

(10) Patent No.: US 12,716,827 B2
(45) Date of Patent: Aug. 25, 2026

(54) SYSTEM AND METHOD FOR DETECTING A TARGET BACTERIA

(71) Applicant: Renascent Diagnostics, LLC, Burlington, VT (US)

(72) Inventor: Matthew D. Gombrich, Burlington, VT (US)

(73) Assignee: Renascent Diagnostics, LLC, Burlington, VT (US)

( * ) Notice: Subject to any disclaimer, the term of this patent is extended or adjusted under 35 U.S.C. 154(b) by 0 days.

(21) Appl. No.: 17/958,896

(22) Filed: Oct. 3, 2022

(65) Prior Publication Data

US 2023/0082300 A1 Mar. 16, 2023

Related U.S. Application Data

(63) Continuation-in-part of application No. 16/779,405, filed on Jan. 31, 2020, now Pat. No. 11,579,069, and (Continued)

(51) Int. Cl.

*G01N 15/1404* (2024.01)
*C12Q 1/18* (2006.01)

(Continued)

(52) U.S. Cl.

CPC ........... *G01N 15/1404* (2013.01); *C12Q 1/18* (2013.01); *G01N 15/1429* (2013.01);

(Continued)

(58) Field of Classification Search

CPC ........... G01N 15/1404; G01N 15/1429; G01N 35/0092; G01N 15/06; G01N 33/48735;

(Continued)

(56) References Cited

U.S. PATENT DOCUMENTS 5,316,905 A * 5/1994 Mori ...................... C12M 29/26 435/297.1
5,576,215 A * 11/1996 Burns ................ G01N 35/0092 422/63

(Continued)

FOREIGN PATENT DOCUMENTS

EP 1936353 A1 * 6/2008 ......... G01N 15/1404
WO WO-2006042439 A1 * 4/2006 ......... G01N 33/1866

(Continued)

OTHER PUBLICATIONS

Translation of WO2015080001A1, Tsuzuki, Yuji, Jun. 4, 2015 (Year: 2015).*

*Primary Examiner* — Henry H Nguyen
(74) *Attorney, Agent, or Firm* — CALDWELL LLC

(57) ABSTRACT

A system for detecting a target bacteria is disclosed. The system comprises a flow cytometer. The flow cytometer is configured to receive a fluid sample, wherein the fluid sample comprises at least a target bacteria and at least a contaminant bacteria. The flow cytometer is also configured to generate a first enumeration of a total bacteria in the fluid sample during a pre-incubation phase. The fluid sample is then incubated during an incubation phase. The flow cytometer then generates a second enumeration of the total bacteria in the fluid sample during a post-incubation phase. A computing device then determines a growth ratio of the total bacteria as a function of the first enumeration and the second enumeration. Finally, the computing device identifies the presence of the at least a target bacteria as a function of the growth ratio.

8 Claims, 9 Drawing Sheets

Related U.S. Application Data a continuation-in-part of application No. 16/096,549, filed as application No. PCT/US2017/029492 on Apr. 25, 2017.

(60) Provisional application No. 62/799,488, filed on Jan. 31, 2019, provisional application No. 62/470,595, filed on Mar. 13, 2017, provisional application No. 62/327,007, filed on Apr. 25, 2016.

(51) Int. Cl.

| | |
|---|---|
| ***G01N 15/01*** | (2024.01) |
| ***G01N 15/06*** | (2024.01) |
| ***G01N 15/10*** | (2024.01) |
| ***G01N 15/14*** | (2024.01) |
| ***G01N 15/1429*** | (2024.01) |
| ***G01N 33/487*** | (2006.01) |
| ***G01N 35/00*** | (2006.01) |

(52) U.S. Cl.

CPC ......... *G01N 35/0092* (2013.01); *G01N 15/01* (2024.01); *G01N 15/06* (2013.01); *G01N 2015/1006* (2013.01); *G01N 2015/1486* (2013.01); *G01N 33/48735* (2013.01); *G01N 2035/00356* (2013.01)

(58) Field of Classification Search

CPC ... G01N 2015/0065; G01N 2015/1006; G01N 2015/1486; G01N 2035/00356; C12Q 1/18

See application file for complete search history.

(56) References Cited

U.S. PATENT DOCUMENTS

| | | | | |
|---|---|---|---|---|
| 6,184,027 B1 * | 2/2001 | Laine | C12Y 302/01017 | 435/261 |
| 7,999,937 B1 * | 8/2011 | Srivastava | B01L 3/502761 | 356/338 |
| 9,657,327 B2 * | 5/2017 | Metzger | C12Q 1/18 | |
| 2003/0072549 A1 * | 4/2003 | Facer | G01N 22/00 | 385/12 |
| 2004/0081906 A1 * | 4/2004 | Kenmoku | C12P 7/625 | 430/108.4 |
| 2005/0123445 A1 * | 6/2005 | Blecka | G01N 35/0099 | 422/64 |
| 2006/0019331 A1 * | 1/2006 | Eden | C12M 41/38 | 422/68.1 |
| 2010/0208960 A1 * | 8/2010 | Kiyota | C12M 41/48 | 382/128 |
| 2011/0151501 A1 * | 6/2011 | Bolea | C12M 23/44 | 435/287.1 |
| 2012/0018334 A1 * | 1/2012 | Baasov | A61P 31/04 | 536/13.2 |
| 2013/0130369 A1 * | 5/2013 | Wilson | G01F 23/26 | 435/289.1 |
| 2014/0252237 A1 * | 9/2014 | Weinstein | C12Q 1/04 | 250/341.8 |
| 2014/0278136 A1 * | 9/2014 | Shamsheyeva | C12Q 1/18 | 702/19 |
| 2015/0064703 A1 * | 3/2015 | Super | G01N 33/56938 | 435/6.12 |
| 2015/0225762 A1 * | 8/2015 | Metzger | C12Q 1/04 | 435/23 |
| 2017/0145378 A1 * | 5/2017 | Ganuza Taberna | A01G 33/00 | |
| 2017/0356028 A1 * | 12/2017 | Motley | C12Q 1/70 | |
| 2018/0237813 A1 * | 8/2018 | Noda | C12N 15/52 | |
| 2018/0259509 A1 * | 9/2018 | Ogbonna | G01N 33/6893 | |

FOREIGN PATENT DOCUMENTS

| | | | |
|---|---|---|---|
| WO | WO-2015080001 A1 * | 6/2015 | C12M 41/36 |
| WO | WO-2016090356 A1 * | 6/2016 | H01J 49/0004 |

* cited by examiner

SYSTEM AND METHOD FOR DETECTING A TARGET BACTERIA

CROSS-REFERENCE TO RELATED APPLICATIONS

This application is a continuation-in-part of Non-provisional application Ser. No. 16/779,405 filed on Jan. 31, 2020, and entitled "METHODS AND SYSTEMS FOR INCREASING THE CAPACITY OF FLOW CYTOMETER BACTERIA DETECTION AND ANTIBIOTIC SUSCEPTIBILITY TESTING SYSTEMS," which claims the benefit of priority of U.S. Provisional Patent Application Ser. No. 62/799,488, filed Jan. 31, 2019, and entitled "METHODS AND SYSTEMS FOR INCREASING THE CAPACITY OF FLOW CYTOMETER BACTERIA DETECTION AND ANTIBIOTIC SUSCEPTIBILITY TESTING SYSTEMS," each of which is incorporated by reference herein in its entirety. This application is also a continuation-in-part of Non-provisional application Ser. No. 16/096,549 filed on Oct. 25, 2018, and entitled "SYSTEMS, DEVICES AND METHODS FOR SEQUENTIAL ANALYSIS OF COMPLEX MATRIX SAMPLES FOR HIGH CONFIDENCE BACTERIAL DETECTION AND DRUG SUSCEPTIBILITY PREDICTION USING A FLOW CYTOMETER," which claims the benefit of priority to PCT Application No. US2017/029492 filed on Apr. 25, 2017, entitled "SYSTEMS, DEVICES AND METHODS FOR SEQUENTIAL ANALYSIS OF COMPLEX MATRIX SAMPLES FOR HIGH CONFIDENCE BACTERIAL DETECTION AND DRUG SUSCEPTIBILITY PREDICTION USING A FLOW CYTOMETER," each of which is incorporated by reference herein in its entirety. Additionally, PCT Application No. US2017/029492 filed on Apr. 25, 2017, entitled "SYSTEMS, DEVICES AND METHODS FOR SEQUENTIAL ANALYSIS OF COMPLEX MATRIX SAMPLES FOR HIGH CONFIDENCE BACTERIAL DETECTION AND DRUG SUSCEPTIBILITY PREDICTION USING A FLOW CYTOMETER." claims the benefit of priority U.S. Provisional Application No. 62/470,595 filed on Mar. 13, 2017, entitled "FLOW CYTOMETER SYSTEMS INCLUDING AUTOMATED FLUID HANDLING SYSTEMS AND METHODS OF USING THE SAME FOR QUANTIFYING THE EFFECTIVENESS OF ANTIMICROBIAL AGENTS," and U.S. Provisional Application No. 62/327,007 filed on Apr. 25, 2016, entitled "ANALYTICAL METHOD FOR ENUMERATIVE COMPENSATION USING A FLOW CYTOMETER," each of which is incorporated by reference herein in its entirety.

FIELD OF THE INVENTION

The present invention generally relates to the field of flow cytometer bacteria detection and antibiotic susceptibility testing systems. In particular, the present invention is directed to a system and method for detecting a target bacteria.

BACKGROUND

Flow cytometer and fluid handling systems may be used for performing quantitative analyses of fluids, such as urine, blood, or cerebral spinal fluid. Any of a variety of quantitative analyses may be performed, such as detection and enumeration of one or more events of interest in a fluid sample.

SUMMARY OF THE DISCLOSURE

In an aspect, a system for detecting a target bacteria is disclosed. The system includes a flow cytometer. The flow cytometer is configured to receive a fluid sample, wherein the fluid sample includes at least a target bacteria and at least a contaminant bacteria. The flow cytometer is also configured to generate a first enumeration of a total bacteria in the fluid sample during a pre-incubation phase, wherein total bacteria includes an aggregate of the at least a target bacteria and the at least a contaminant bacteria. The fluid sample is then incubated during an incubation phase. The flow cytometer then generates a second enumeration of the total bacteria in the fluid sample during a post-incubation phase. A computing device then receives the first enumeration and the second enumeration. The computing device then determines a growth ratio of the total bacteria as a function of the first enumeration and the second enumeration. Finally, the computing device identifies the presence of the at least a target bacteria as a function of the growth ratio.

In another aspect, a method for detecting a target bacteria is disclosed. The method includes receiving, at a flow cytometer, a fluid sample, wherein the fluid sample includes at least a target bacteria and at least a contaminant bacteria. The method includes generates, at the flow cytometer, a first enumeration of a total bacteria in the fluid sample during a pre-incubation phase, wherein total bacteria includes an aggregate of the at least a target bacteria and the at least a contaminant bacteria. Additionally, the method incubates, at the flow cytometer, the fluid sample during an incubation phase. The method includes generating a second enumeration of the total bacteria in the fluid sample during a post-incubation phase. The method includes receiving, at a computing device, the first enumeration and the second enumeration. The method includes determining, at the computing device, a growth ratio of the total bacteria as a function of the first enumeration and the second enumeration. Finally, the method identifies, at the computing device, the presence of the at least a target bacteria as a function of the growth ratio.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for detecting a target bacteria. The system includes a flow cytometer. The flow cytometer is configured to receive a fluid sample, wherein the fluid sample includes at least a target bacteria population and at least a contaminant bacteria population. The flow cytometer is also configured to generate a first enumeration of a total bacteria in the fluid sample during a pre-incubation phase, wherein total bacteria includes an aggregate of the at least a target bacteria and the at least a contaminant bacteria. The fluid sample is then incubated during an incubation phase. The flow cytometer then generates a second enumeration of the total bacteria in the fluid sample during a post-incubation phase. A computing device then receives the first enumeration and the second enumeration. The computing device then determines a growth ratio of the total bacteria as a function of the first enumeration and the second enumeration. Finally, the computing device identifies the presence of the at least a target bacteria as a function of the growth ratio. Exemplary embodiments illustrating aspects of the present disclosure are described below in the context of several specific examples.

Figure 1:
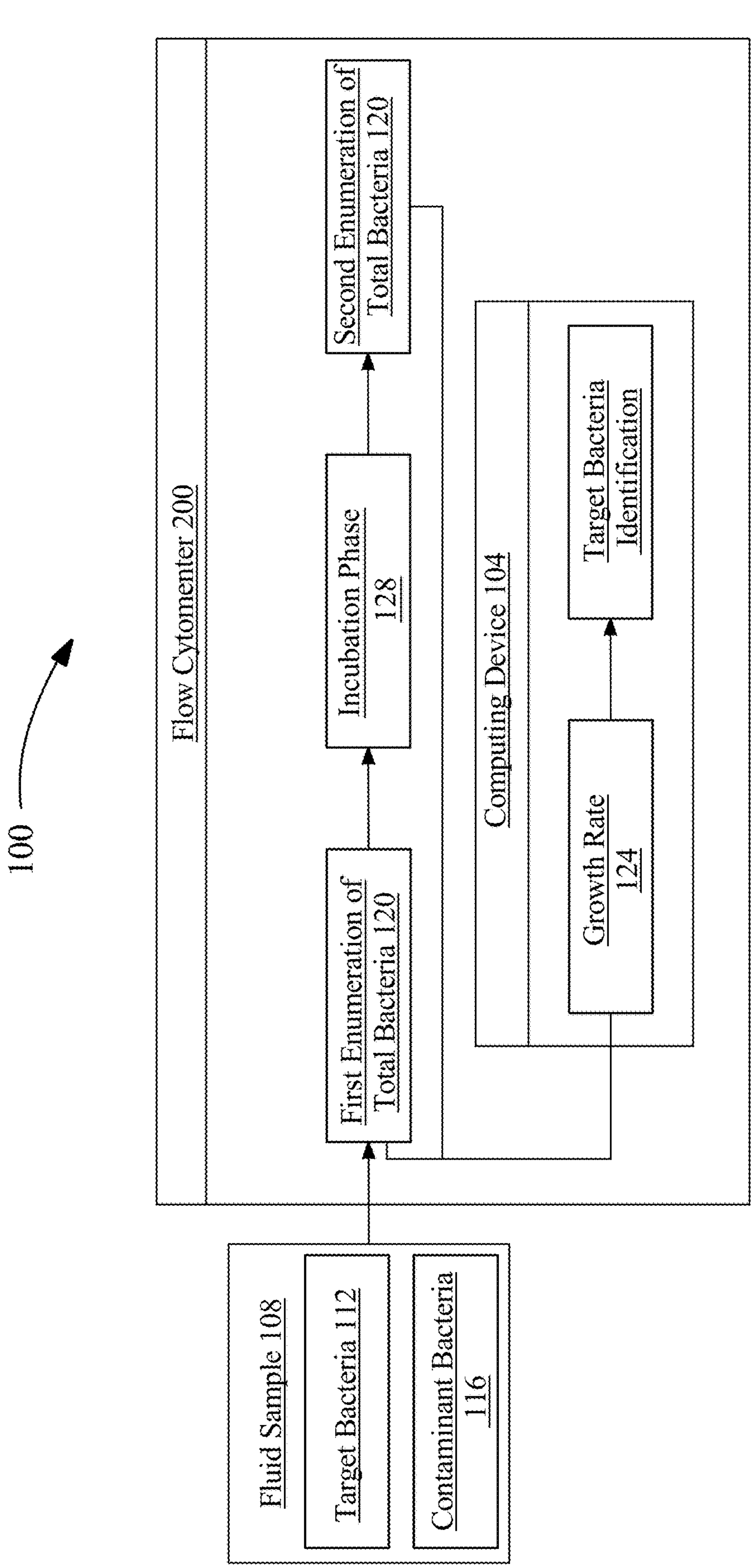
FIG. 1 is a block diagram of an exemplary system for detecting a target bacteria.

Referring now to FIG. 1, an exemplary embodiment of a system 100 for detecting a target bacteria is illustrated. System 100 includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. computing device 104 may include but is not limited to, for example, a computing device or cluster of computing devices in a first location and a second computing device or cluster of computing devices in a second location. computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 1000 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, a flow cytometer may be configured to receive a fluid sample 108. As used in the current disclosure, a "fluid sample" is a sample that may require physical or chemical analysis. Examples of a fluid sample may include spinal fluid, urine, blood, saliva, and a plurality of other bodily fluids. A fluid sample includes at least a target bacteria 112 population and at least a contaminant bacteria population 116. As used in this disclosure, "target bacteria" are the bacteria that is of interest during the process. Target bacteria may include a pathogenic bacteria. As used in this disclosure, "contaminant bacteria" are any other cells or bacteria other than the target bacteria 112 that may be present in a sample. A fluid sample may be configured to be housed within a multi-well cassette, as discussed in greater detail herein below in FIG. 3.

With continued reference to FIG. 1, a fluid sample 108 concentration may be diluted or adjusted the by addition of appropriate amounts of growth media as a function of a dilution factor. A "growth media" as used in the current disclosure, is a solid, liquid, or semi-solid designed to support the growth of a population of micro-organisms or cells via the process of cell proliferation. Different types of growth media are used for growing different types of cells. In embodiments, the growth media may be a complex growth media or a synthetic growth media. Wherein, a complex growth media contains ingredients whose exact chemical composition is unknown (e.g. blood, yeast extract, etc.) and a synthetic growth media are formulated to an exactly defined chemical composition. The growth media for bacteria may include nutrient broths, agar plates, Tryptic Soy Agar (TSA), Chocolate Agar, Thayer-Martin Agar, MacConkey (lactose) Agar, Eosin-methylene Blue Agar (EMB), Hektoen Agar, Mannitol Salt Agar, Triple Sugar Iron Agar (TSI), and the like. In some cases, a specialized media are sometimes required for microorganism and cell culture growth. Types of growth media may include a culture media, minimal media, selective media, differential media, transport media, and the like. In embodiments, dilution of a fluid sample 108 may occur prior to the incubation period. As used in the current disclosure, "dilution" is the process of decreasing the concentration of a solute in a solution, usually simply by mixing with more solvent like adding more water to the solution. To dilute a fluid sample 108 may mean adding more growth media without the addition of more fluid sample 108. The resulting solution may be thoroughly mixed so as to ensure that all parts of the solution are identical. As used in the current disclosure, a "dilution factor" is a ratio used to express how much of the original stock solution is present in the total solution, after dilution. In some embodiments, a dilution factor may be represented as an exponent. Regardless if dilution factor is a ratio or exponent, it has two forms, either describing the parts of the solute to the parts of the dilutant/growth media added or the parts of the solute to the parts of the total solution. In a non-limiting example, this may include a ratio of the fluid sample 108 to the growth media contained in the solution. In other embodiments, this may include the ratio of a fluid sample 108 to the total volume of the diluted fluid sample.

With continued reference to FIG. 1, a flow cytometer may be configured to generate a generate an enumeration of total bacteria 120 in the fluid sample 108. As used in the current disclosure "enumeration of total bacteria" is the counting of the number of bacteria within a given sample. Enumeration of total bacteria 120 within fluid sample 108 may be expressed as a number of cells per unit of volume, thus expressing a concentration (for example, 5,000 cells per milliliter). The flow cytometer may be the same or substantially similar to the flow cytometer of those discussed herein below in FIG. 2. As used in the current disclosure, "total bacteria" includes an aggregate of the at least a target bacteria 112 and the at least a contaminant bacteria 116. Bacterium types may be differentiated by staining, and include, without limitation viable, non-viable, gram-positive, and the like. In an embodiment, a flow cytometer may be configured to produce enumerations of a target bacteria 116 and a contaminant bacteria 116 separately. A flow cytometer may be configured to generate a first enumeration of total bacteria during a pre-incubation phase. As used in the current disclosure, a "pre-incubation phase" is the time period prior to incubation. A flow cytometer may also be configured to generate a second enumeration of total bacteria during the post-incubation phase. As used in the current disclosure, a "post incubation phase" is the time period after incubation. Both the pre-incubation phase and a post-incubation phase are discussed in greater detail herein below in FIG. 2.

With continued reference to FIG. 1, a flow cytometer may be configured to incubate the fluid sample during an incubation phase 128. As used in the current disclosure, a "incubation phase" is a period of time in which the fluid sample 108 is being incubated. In embodiments, the time of the incubation phase 128 may be calculated as a function of an incubation parameter. As used in the current disclosure, an "incubation parameter" is a parameter associated with incubation. For example, incubation parameter may include an amount of time that is required during the incubation phase 128. Exemplary non-limiting incubation parameters include growth media type, incubation temperature, agitation parameters, change and rate of change in temperature, duration of incubation, and the like. In some cases, incubation parameter may be selected as a function of target bacteria. For example, temperature, duration, growth media, and the like may all be selected to foster increased growth of target bacteria relative contaminant bacteria. An incubation parameter may be calculated as a function of the type of target bacteria 112, fluid sample 108, and contaminant bacteria 116. In a non-limiting example, it may take 12-18 hours for target bacteria 112 to be fully incubated. As another non-limiting example, when target bacteria 112 is suspended in a fluid sample 108 of urine the incubation parameter may be 14 hours.

With continued reference to FIG. 1, computing device 104 may generate an incubation parameter using a look up table. A "lookup table," for the purposes of this disclosure, is an array of data that maps input values to output values. A lookup table may be used to replace a runtime computation with an array indexing operation. In another non limiting example, an incubation parameter look up table may be able to relate an incubation parameter to a target bacteria 112, fluid sample 108, and contaminant bacteria 116. Computing device 104 may be configured to "lookup" one or more a target bacteria 112, fluid sample 108, and contaminant bacteria 116, and the like, in order to find a corresponding incubation parameter.

With continued reference to FIG. 1, a flow cytometer may be the same or substantially similar to flow cytometer 200, as discussed in greater detail herein below in FIG. 2. As used in the current disclosure, a "flow cytometer" is a machine configured to count or similarly quantify the number of cells in a sample, wherein the cells are suspended in a fluid. A flow cytometer may include an image cytometer, flow cytometer, cell sorters, a time lapse cytometer, a Coulter counter, and the like. The bacteria may be counted using the Coulter principal. In the Coulter principal the cells, swimming in a solution that conducts electricity, are sucked one by one into a tiny gap. Flanking the gap are two electrodes that conduct electricity. When no cell is in the gap, electricity flows unabated, but when a cell is sucked into the gap the current is resisted. The Coulter counter counts the number of such events and also measures the current (and hence the resistance), which directly correlates to the volume of the cell trapped. A similar system is the CASY cell counting technology. In embodiments, cells may be sorted using technology similar to what is used in inkjet printers. The fluid stream is broken up into droplets by a mechanical vibration. The droplets are then electrically charged according to the characteristics of the cell contained within the droplet. Depending on their charge, the droplets are finally deflected by an electric field into different containers.

With continued reference to FIG. 1, a flow cytometer may be configured to count the number of a cells within a sample using a fluorescent system. A fluorescent system uses a system of laser to target the cell of interest and plurality detectors to convert the emitted light for the cell into a digital signal. The digital signal may then be used to count or similarly quantify the number of cells in a sample. A fluorescent system may bring the cells to the integration point. The integration point is the point where a laser contacts the cell. In embodiments, the laser may be coherent (has a synchronized, identical wave frequency), monochromatic (has a single wavelength), and energetic. These properties may ensure that the cells are illuminated with uniform light of a specific wavelength. The laser may be included as a portion of the optical system flow cytometer. The components of the optical system include excitation light sources, lenses, and filters used to collect and move light around the instrument, and the detection system that generates the photocurrent. The components of the optical system may work in concert to use a laser to shine different wavelengths of light onto the cell, collect the data (i.e. side and forward scatter as well as emission from the excited fluorophores) in the form of emitted photons and convert these photons to an electrical signal—a photocurrent—that goes into the electronics system. In some embodiments, in an effort to make the measurement of biological/biochemical properties of interest easier, the cells may be stained with fluorescent dyes which bind specifically to cellular constituents. The dyes may be excited by the laser beam, and emit light at longer wavelengths. This emitted light is picked up by detectors, and these analogue signals are converted to digital so that they may be stored, for later display and analysis. The electronics system may be responsible for the conversion of emitted light signals to a measurable electronic signal, and then measuring, amplifying, and digitizing that signal to be communicated to the computing device 104.

With continued reference to FIG. 1, a computing device 104 may be configured to receive both a first and second enumeration of total bacteria 120. A computing device may be configured to determine a growth ratio 124 of the total bacteria as a function of the first and the second enumeration. As used in the current disclosure, a "growth ratio" is a measure of growth of bacteria, for example growth ratio may be a rate of growth of total bacteria. In an embodiment, a rate of growth may be determined by comparing the number of total bacteria in the first enumeration compared to the second enumeration. A growth ratio 124 may be displayed as percentage or ratio of growth between the first enumeration and the second enumeration. A comparison may be conducted by subtracting the first enumeration from the second enumeration. In so some embodiments, a computing device 104 may be configured to calculate the growth ratio 124 specifically of a target bacteria 116 and/or a contaminant bacteria 116. The process of calculating the growth ratio 124 may be discussed in greater detail, herein below in FIG. 4.

With continued reference to FIG. 1, a computing device 104 may identify the presence of the at least a target bacteria 116 as a function of the growth ratio 120. Different target bacteria 116 exhibit different growth ratios. For example, pathogenic bacteria, non-pathogenic bacteria, contaminant bacteria may each exhibit different growth ratios according to different incubation parameters. For example, it has been determined that target bacteria 116 in human urine exhibit a growth ratio that is approximately 5×±1 greater than the growth ratio of contaminant cells when cultured over short culture times in the range of approximately 2.5 hours. It may be possible in certain circumstances to state the growth ratio difference more specifically as 5×±0.5. Thus in one embodiment, if the T1 to T0 target bacteria 116 growth ratio is determined to be between about 6.25× and 16.25× (i.e., about 125% to about 325%) the sample may be assessed as a positive for pathogenic bacteria. More disclosure is provided herein below in FIG. 4.

With continued reference to FIG. 1, a computing device 104 may determine a diagnosis as a function of the growth ratio 120 and one or more of the first enumeration and the second enumeration. In embodiments, a computing device 104 may be configured to compare the first enumeration, second enumeration, and the growth ratio to generate a diagnosis of the sample. A diagnosis may be the determination that human that the fluid sample originated from has an illness or other problem. In a non-limiting example, a computing device 104 may determine that a user has a urinary tract infection as a function of the growth ratio 120 of the target bacteria and the number of target bacteria as enumerated within the second enumeration with a fluid sample 108 comprised of urine. Computing device 104 may generate a diagnosis using a look up table. In a non-limiting example, a diagnosis look up table may be able to relate a diagnosis to a first enumeration, second enumeration, growth ratio 120, fluid sample 108, and contaminant bacteria 116. Computing device 104 may be configured to "lookup" one or more first enumeration, second enumeration, growth ratio 120, fluid sample 108, contaminant bacteria 116 and the like, in order to find a corresponding diagnosis.

Figure 2:
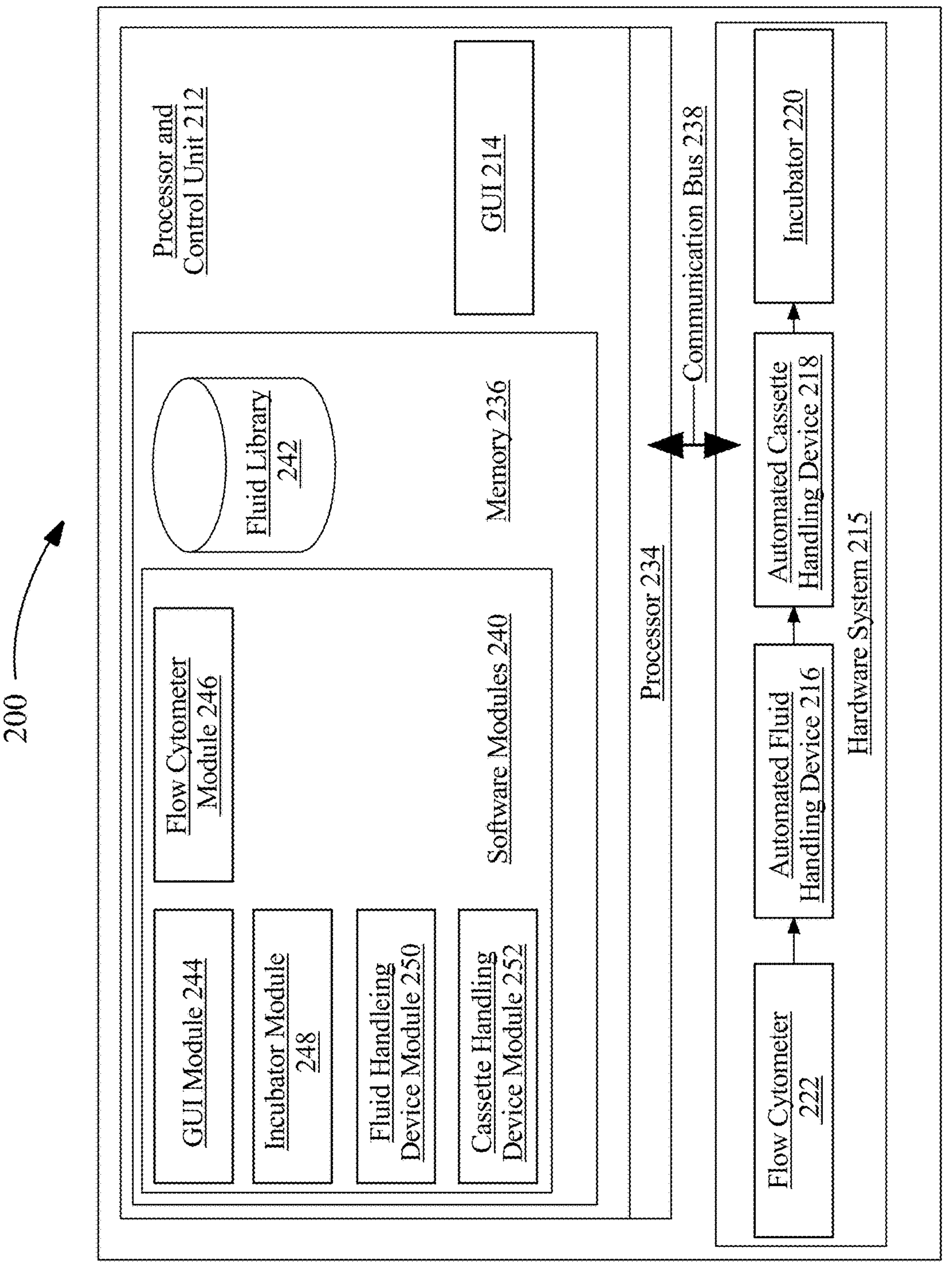
FIG. 2 is a block diagram of an automated flow cytometry and fluid handling system made in accordance with the present disclosure.

FIG. 2 illustrates an exemplary embodiment of a flow cytometer and fluid handling system 200 which includes processing and control unit 212 with a graphical user interface (GUI) 214 to allow a user to control operation of system hardware components. Hardware system 215 may include hardware components such as fluid handling system 216, automated cassette handling system 218, incubator 220 and flow cytometer 222. As described more below, flow cytometer 222 performs a variety of measurements on clinical fluid samples, however, it can only analyze one clinical sample at a time. In one example, a multi-well cassette (FIG. 2) may be used to hold multiple samples. Fluid handling system 216, automated cassette handling system 218, and incubator 220 may include one or more robotic components controlled by processors (e.g. processor 234), and may be designed and configured to automatedly transport multi-well cassettes 1200 between incubator 220 and flow cytometer 222 and transport clinical samples from a given cassette to the flow cytometer for analysis. Fluid handling system 216 may include, for example, an automated pipetting system, as well as one or more cassette handling robots and microplate washers. Automated cassette handling system 218 may be configured to transport cassettes between fluid handling system 216 and incubator 220. In some examples, automated cassette handling system 218 may be omitted and cassettes may be manually transported between fluid handling system 216 and incubator 220. As will be appreciated, the number of one or more of components in hardware system 215 may vary. For example, one or more of fluid handling system 216, automated cassette handling system 218, and incubator 220 may be configured to function with only one flow cytometer 222, or a plurality of flow cytometers.

Processing and control unit 212 may comprise processor 234 and memory 236. The memory and processor communicate with GUI 214 and hardware system 215 through appropriate application programming interfaces (API) and communication buses 238. Configurations with respect to processor communication and control are described in more detail below with respect to FIG. 5. Components of memory 236 may include software modules 240 configured specifically to control and operate the connected hardware components and fluid library 242. Exemplary software modules may comprise GUI module 244, flow cytometer module 246, incubator module 248, fluid handling device module 250, and cassette handling device module 252. Fluid library 242 is populated with fluid and bacteria specific information used for analyzing the particular type of fluid under analysis, such as, but not limited to, urine, spinal fluid, and blood. For example, flow cytometer software module 46 may access pre-defined regions of interest (ROIs), scatter values and fluorescence values etc. stored in the fluid library for detecting various species of bacteria in various fluids being tested. Detections in the ROI possessing characteristics of target events, such as scatter values and fluorescence values, as determined by gating strategies and/or computational analysis executed by the flow cytometer software may be used to determine concentration of particles, cells, or bacteria of interest in the sample.

Figure 3:
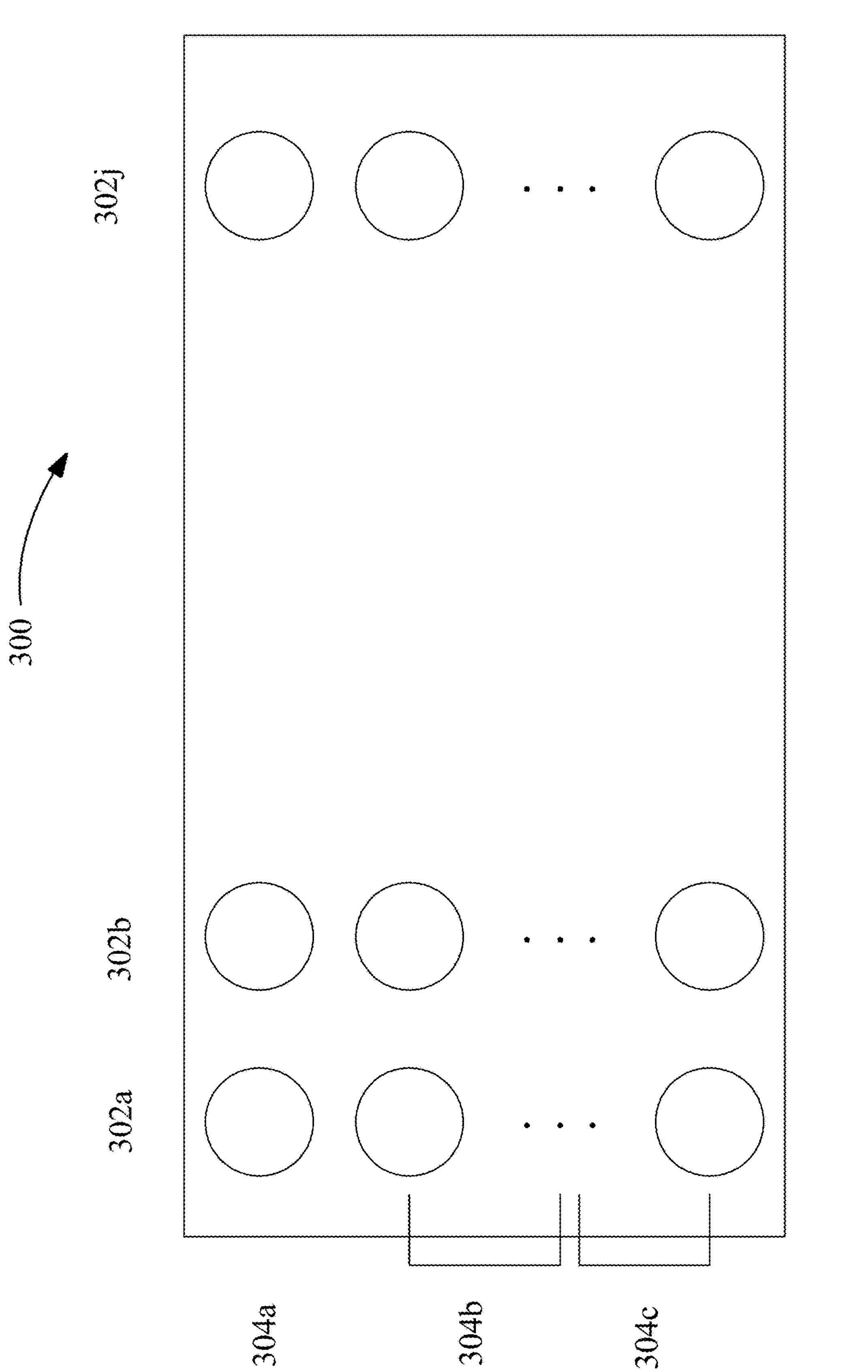
FIG. 3 is an example multi-well cassette that may be used for performing methods of the present disclosure.

FIG. 3 illustrates an example multi-well cassette 300 for holding a plurality of clinical fluid samples for analysis by flow cytometer(s) 222. Cassette 300 includes a plurality of columns 302 *a*-302 *j* of wells, each column including a plurality of wells 304. In this example, "j" is a variable indicating that any number of columns may be used. In one example, separate clinical fluid samples are initially deposited in the first row (wells 304 *a*) of each column 302 and the first row of wells are then used as a reservoir for drawing portions of the fluid sample for further processing and analysis by system 100. For example, if j=6, meaning cassette 300 includes six columns 302, six different fluid samples, e.g., urine samples from, e.g., six different patients, can be loaded into cassette 300 for automated processing.

Figure 4:
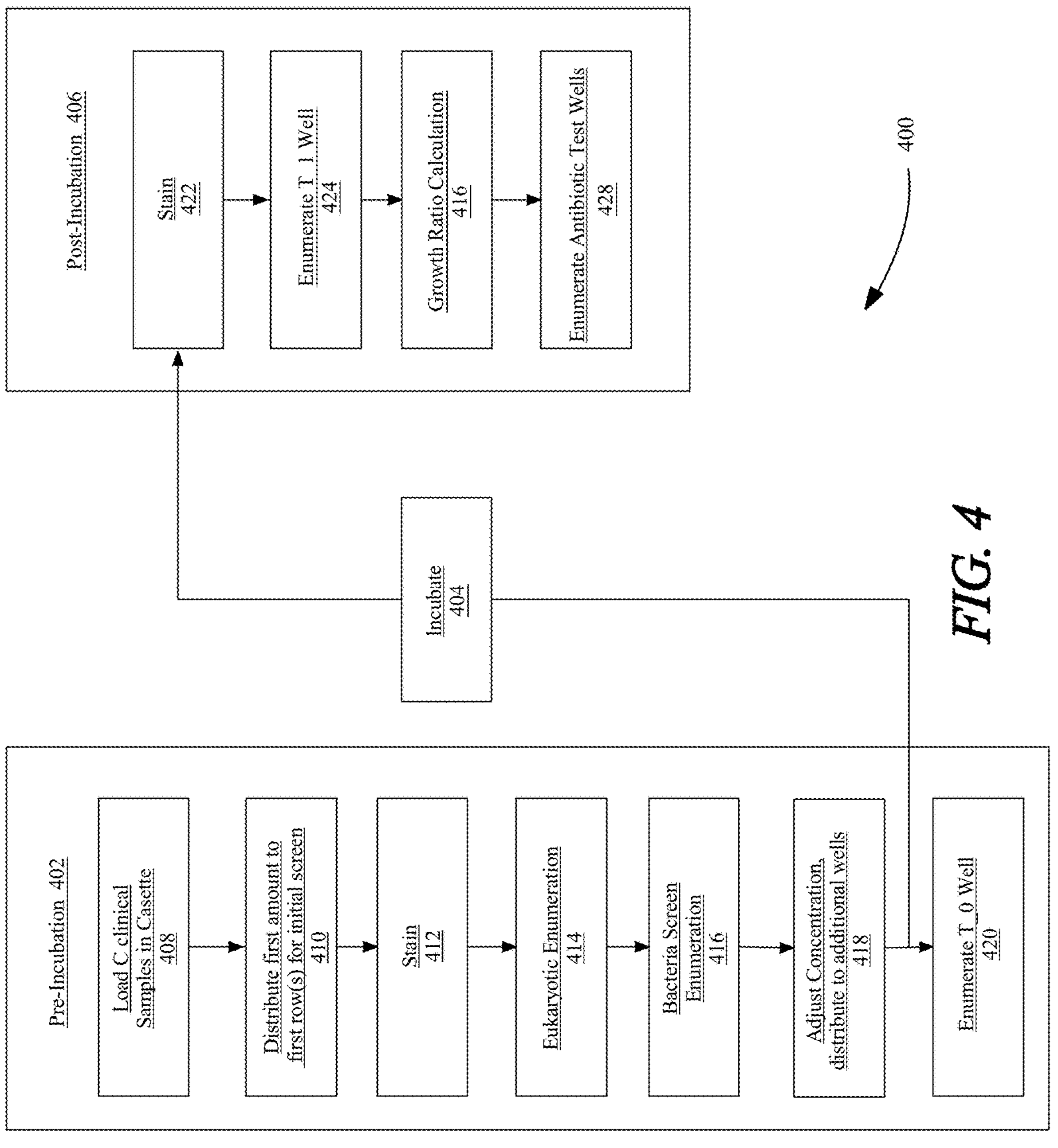
FIG. 4 is an example process for analyzing a multi-well cassette for rapid determination of bacterial infection and antibiotic susceptibility.

FIG. 4 illustrates an example process 400 for analyzing a single multi-well cassette 300 with system 100. In one exemplary embodiment, process 400 includes three phases a pre-incubation phase 402, where an initial screening analysis is performed on one or more clinical samples to determine, for example, whether one or more samples contain a bacterial infection, an incubation phase 404, where one or more clinical samples are incubated for a specific period of time, and a post-incubation phase 406, where one or more samples are analyzed to verify the sample contains an infection of pathogenic bacteria and to identify one or more antibiotics that may be effective in combating the pathogenic bacteria population(s).

Pre-incubation phase 402 may begin at step 408, with a single volume of a sample being loaded in the first row 304 *a* of cassette 300. For a cassette containing j columns of wells, j samples may be loaded in the first row 304 *a* of corresponding respective columns 302 *a-j*. Cassette 300 may have a predetermined volume of growth media, e.g., 1 ml, in one or more media wells. In one example, Mueller Hinton Broth may be used as the growth media. Fluid handling system 216 may contain one or more wells, volumes, or containers, with dyes, staining agents, control beads, and antibiotics for use during an automated analysis process.

At step 410, after j samples are loaded in row 304 *a*, fluid handling system 216 may utilize automated pipetting system or other suitable probe to remove, e.g., aspirate, a predetermined amount of each sample to row(s) in row group 304 *b* for pre-incubation analysis. In one example, row group 304 *b* include two rows. At step 412, fluid handling system 216 may obtain appropriate cellular stains from designated positions in the fluid handling system and stain the fluid samples in rows 304 *b*. In some embodiments, the dyes may include at least two different dyes, for example one dye that permeates only dead cells, e.g., propidium iodide, and another that permeates all cells, e.g., thyzol orange. Using distinct dye types in this manner allows for discrimination between live and dead cells based on the different fluorescence characteristics of the different dyes when interrogated by appropriate excitation light sources(s).

At step 414, fluid handling system 216 may then deliver the contents of a first well, e.g., a first row 304 *b* of a first column 302 *a* to flow cytometer 222 for a first analysis, e.g., eukaryotic enumeration. The analysis may include scatter plots and fluorescence plots that include gates for red and white blood cell counts. This analysis enables accurate enumeration of specific cell populations that may provide clinically relevant information for the disease process being screened. As an example, the presence of white blood cells in urine samples being screened for urinary tract infections is a secondary indicator of active infection, beyond the presence of bacteria.

In one embodiment, next, at step 416, contents of one sample column 302 in a second row in row group 304 *b* are delivered by fluid handling system 216 to flow cytometer 222 for bacteria screen enumeration. Scatter plot gating and fluorescence intensity analysis may again be used to determine a bacteria count corresponding to events falling within an ROI. The bacteria screen count of step 416 may utilize the live/dead cell staining applied at step 412 to exclude dead cells from the bacteria enumeration. The live bacteria cell enumeration can be compared to predetermined threshold values to assess whether continued analysis of the sample is warranted. For example, current clinical standards relative to assessment of urinary tract infections indicate thresholds of 104/ml or 105/ml depending on factors such as clinical status of the patient. Other threshold values may be applied as appropriate for analysis of other clinical indications or other clinical situations.

It should be noted that while the bacteria screen step 416 may be conducted to largely eliminate dead cells from the cell count based on use of fluorescence discriminating dyes, cell count at this stage may still include all types of live cells, both live cells of interest and live cells that are not of interest that may thus be considered as contaminant cells. For example, in assessment of urinary tract infections, a primary pathogenic bacterium of interest is *E. coli*. However, a typical human urine sample may also include many different species of non-pathogenic flora. These non-pathogenic flora may be considered as contaminants with respect to accurate clinical analysis of pathogens.

Thus, after completion of step 416 system 100 may stop analyzing samples in one or more of columns 302. For example, the bacteria count determined at step 416 for one or more of the samples initially loaded in columns 302 *a-j* may have a bacteria count below the applicable threshold, indicating the sample does not meet a clinical definition of a bacterial infection.

Based on bacterial count determined in the preceding steps, in step 418 sample concentration is adjusted to a target bacterial level and samples distributed from row 304 *a* to row group 304 *c* for further analysis. In one example, this step is omitted for any sample(s) that system 100 determined at step 416 did not contain a live bacteria count above the applicable threshold. As is known in the art, testing of bacteria for antibiotic resistance or susceptibility typically requires a bacterial concentration in the range of approximately 1×10^5 to approximately 1×10^6 bacteria/ml. However, depending on the sensitivity and accuracy of the instrumentation employed (for example some flow cytometer systems are more sensitive than others), lower concentrations may be employed. Thus, methods of the present disclosure may be employed with concentrations as low as in the range of 1×10^3 bacteria/ml. For example, instrument sensitivity may indicate a concentration in the range of approximately 1×10^4 bacteria/ml to approximately 5×10^4 bacteria/ml, or other instrumentation may employ a concentration in the range of approximately 1×10^3 bacteria/ml to approximately 5×10^3 bacteria/ml. Various antimicrobial efficacy testing methods may require a standard concentration of bacteria, e.g., a predetermined bacterial concentration of 1×10^5 bacteria/ml.

Adjustment of sample concentration at step 418 can be accomplished by addition of appropriate amounts of growth media when samples are further distributed by fluid handling system 216. If initial testing of a clinical sample indicates a higher concentration, e.g., if the flow cytometer enumerates an initial sample at 1×10^7 bacteria/ml, the system may automatically adjust the concentration for subsequent testing. In one example, 1 microliter of the sample may be aspirated by the fluid handling system and deposited into 1000 microliters of media in a first one of media wells 304 *c* to arrive at the target concentration of 1×10^4. In another example, the initial concentration may be greater than 1×10^7 bacteria/ml, and/or the minimum aspiration volume may be greater than 1 microliter, and/or the target concentration may be lower, etc. such that a second dilution step is required. The fluid handling system may be configured to determine a second amount of fluid to be aspirated from the first media well containing media and the first amount of the fluid sample for deposit in a second media well in group 304 *c* to arrive at the target concentration, e.g., 1×10^4 bacteria/ml.

Sample distribution at step 418 includes distribution of a time zero control, TO, sample to a first well in group 304 *c* as well as a T1 sample to a second well in group 304 *c*. Optionally further samples may be distributed to antibiotic testing (AT) well(s) in group 304 *c*. In one embodiment, adjustment step 418 is accomplished by depositing a properly diluted sample in an initial well in group 304 *c* and then distributing an amount of the properly-diluted sample from the initial well to all other wells to be employed.

At step 420, a first sample, referred to herein as a TO sample, from the properly-diluted samples in group 304 *c*, is transported to flow cytometer 222 to obtain a baseline time-zero bacteria count. After removing a portion of the TO sample from cassette 300 for enumeration, at step 404 the cassette 300 containing a second sample for enumeration after incubation, the T1 sample, and any desired antibiotic testing samples is delivered to incubator 220 by automated cassette handling system 218 and incubated. AT wells in group 304 *c* may be prefilled with specific antibiotics against which testing is to be run or may be separately filled from an appropriate source by the fluid handling system. Incubation time will depend on the nature of the cells to be studied. For example, with respect to cells of interest, such as urogenital flora, incubation time may be in the range of about 2.5 hours, or typically less than about 3 hours, but more than 2 hours. As described more below, in some examples, it can be very important that each cassette 300 containing the same type of fluid sample is incubated for the same period of time.

After incubation, at step 422, the multi-well cassette is returned to fluid handling system 216 by automated cassette handling system 218. At step 422, all T1 samples and AT wells in group 304 *c* are stained by fluid handling system 216. In one example, the same live/dead stains that were used in step 412 are used here. Thereafter, at step 424 T1 samples are enumerated and the growth ratio after incubation, i.e., ratio of T1 to T0 cells, is determined at step 426.

Enumeration (416, 424) and assessment of the T1/T0 cell growth ratio (426) are important steps to allow quantitative discrimination between pathogenic cells/bacteria of interest and contaminant cells/bacteria. It has been determined by the Applicant that pathogenic bacteria exhibit different growth ratios as compared to non-pathogenic, contaminant bacteria and that these differences in growth ratio may be used to discriminate qualitatively between cells of clinical interest and contaminant cells, without reliance on more subjective measures such as species identification using chemical means or matrix assisted laser desorption/ionization time of flight mass spectrometry (MALDI-ToF). For example, it has been determined that pathogenic cells in human urine exhibit a growth ratio that is approximately 5×±1 greater than the growth ratio of contaminant cells when cultured over short culture times in the range of approximately 2.5 hours. It may be possible in certain circumstances to state the growth ratio difference more specifically as 5×±0.5. Thus in one embodiment, if the T1 to T0 cell growth ratio is determined to be between about 6.25× and 16.25× (i.e., about 125% to about 325%) the sample may be assessed as a positive for pathogenic bacteria.

In another embodiment, the system may be programed to convert the relative growth between T0 and T1 to an integer representing bacterial population expansion. In such an embodiment, the derived growth integer from T0 baseline to T1 control growth is compared to the known growth integers of a known library of pathogens represented in the disease state being tested. Representative disease states may include, but are not limited to, pathogens associated with urinary tract infections, pathogens associated with blood stream infections (bacteremia/sepsis), pathogens associated with meningitis or other neurologic infections. Alternatively or additionally, the derived growth integer is compared to the known growth integers of a known library of possible bacterial contaminants represented in the disease state being assessed, such as, but not limited to normal urogenital flora associated with suspected urinary tract infections or possible skin contaminant associated with blood sampling in suspected bacteremia samples. Known libraries of pathogens and contaminants may be stored in fluid library 242 in memory 236.

Depending on the clinical objective, for example if simply determining existence of a urinary tract infection is the goal, then the positive result may be the stopping point and the result reported to the appropriate health care provider or patient. However, embodiments of the present disclosure also provide for rapid assessment of antibiotic resistance/susceptibility prediction if such information is desired. If the result of the assessment in step 426 is positive, enumeration of the samples placed in the AT wells may proceed. Because the samples were distributed to the AT wells at the same time as the T0 and T1 wells, the samples in the AT wells were cultured also during incubation step 404 and thus may be immediately enumerated without additional culture time. At step 428, samples from AT wells in group 304 *c* for each of columns 302 that tested positive at steps 416 and 426 are enumerated to determine an antibiotic prediction profile or for use as information in determining antibiotic susceptibility based on comparison with the T1 sample. For these comparisons, the T1 enumeration provides a baseline against which the AT well enumeration is compared. Resistance prediction may be based on growth ratio thresholds as may be established for specific clinical indications and/or drugs and antibiotics. Note that once again, by using flow cytometer enumeration and comparing the ratio of, e.g., ATn/T1, a quantitative measurement of the antibiotic/drug effectiveness may be determined.

Automated flow cytometry systems made in accordance with the present disclosure can be configured to process a plurality of multi-well cassettes, such as multi-well cassette 300, each of which may contain a plurality of different fluid samples. As described above in connection with FIG. 4, the analysis of each cassette includes three phases—a pre-incubation phase 402, an incubation phase 404, and a post-incubation phase 406. After system 100 performs pre-incubation phase 402 on a first cassette and the first cassette is deposited in incubator 220, the first cassette will need to remain in the incubator for a relatively long time, e.g., three hours. System 100 can, therefore, begin the pre-incubation phase 402 for a second cassette, however, as noted above, it is important that post-incubation phase 406 begins substantially immediately after reaching the required incubation time because the growth ratio calculations performed at steps 426 and 428 and determinations of infection and antibiotic effectiveness are based on a pre-determined incubation time and temperature.

Figure 5:
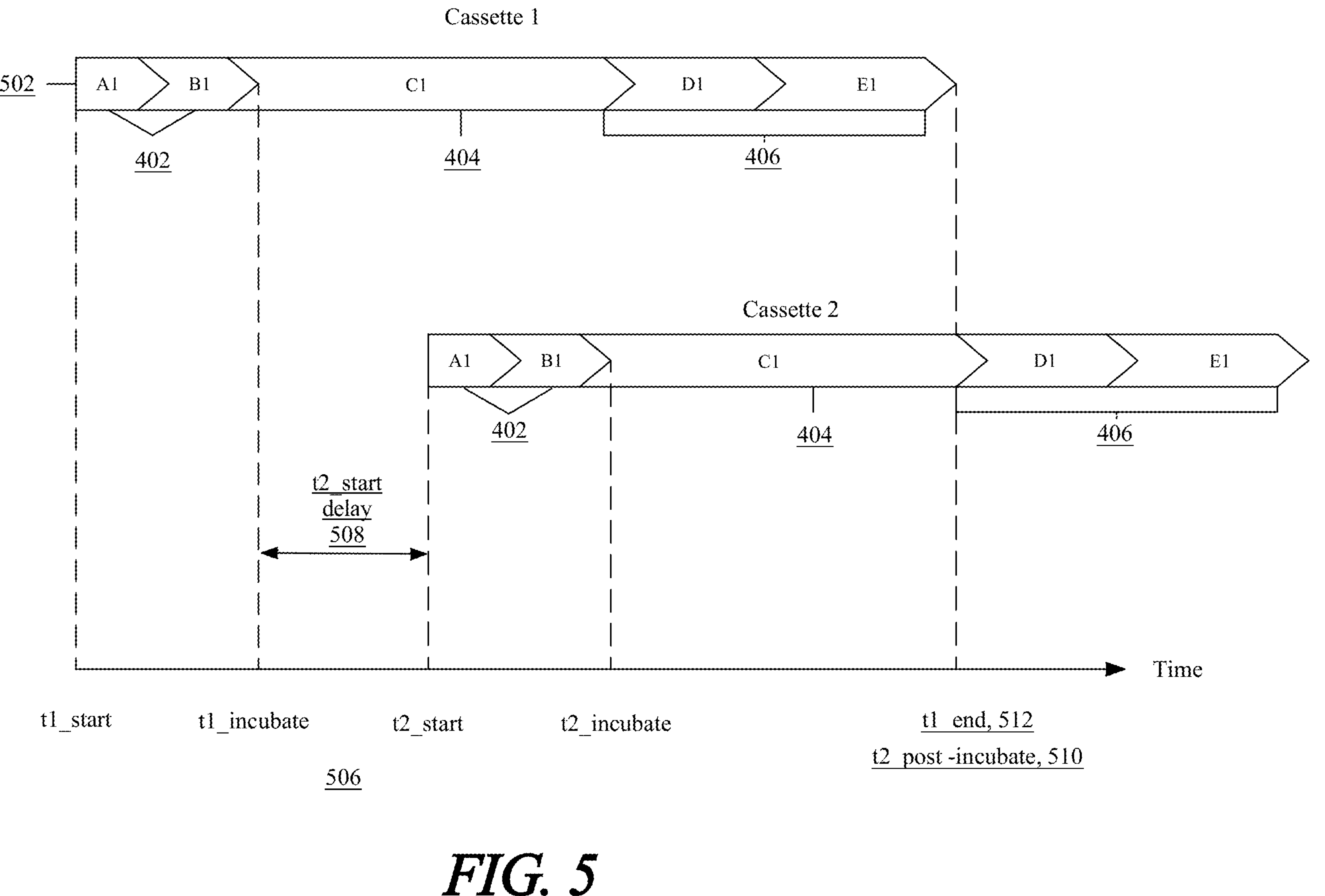
FIG. 5 is an example timeline for sequentially processing a plurality of multi-well cassettes, each cassette containing a plurality of clinical fluid samples.

This time dependency between the analysis of sequential cassettes is illustrated in FIG. 5, which shows a timeline 502 for analysis of a first cassette and a timeline 504 for analysis of a second cassette. Pre-incubation phase 402 includes a first period A that represents a portion of the pre-incubation phase through an initial live bacteria enumeration, e.g., steps 408-416. Second period B, which is the amount of time required to perform a pre-incubation process on x clinical samples of a cassette after an initial live bacteria enumeration, e.g., steps 418-420. As noted above, after the initial bacteria screen at step 416, system 100 may be configured to only continue to process the samples that have a live bacteria count that exceeds a pre-determined threshold, such that time period B of pre-incubation phase 402 may vary from cassette to cassette.

Timelines 502, 504 also include the incubation phase Cl 404, and contain post-incubation phase 406, which include a first period, D, which represents the amount of time after incubation through performing a growth ratio determination process, e.g., steps 422-426. Post-incubation phase 406 may also include a second period, E, which is the amount of time required to perform a bacteria susceptibility determination process, e.g., step 428. As noted above, in some examples, system 100 may be configured to only perform step 428 to analyze the AT wells for samples that meet or exceed a threshold ratio determined in step 426.

As shown conceptually in FIG. 5, system 100 may need to delay the start of the second cassette, t2_start 506 by a delay time t2_start delay 508 to ensure the beginning of post-incubation phase 406 for cassette 2 (t2_post-incubate 510) does not occur prior to the end of post-incubation phase 406 for cassette 1 (t1_end 512). Incorporating any required delay prior to analysis of cassette 2 ensures flow cytometer 222 has completed the post-incubation phase 406 for a first cassette and is available to begin the post-incubation phase 406 of a second cassette. As noted above, this can be important for ensuring the accuracy and reliability of the measurements and analytical results for the second cassette. As will be appreciated, FIG. 5 is a simplified conceptual illustration of only two cassettes, however, system 100 can be configured to concurrently process a significantly greater number of multi-well cassettes, with a plurality of the cassettes undergoing incubation phase 404 in incubator 220 at the same time. The relationship illustrated in FIG. 5 applies to any two sequential cassettes. Also, the relative durations of the phases illustrated in FIG. 5 are not drawn to scale. For example, incubation phase 404 may be a longer duration relative to pre and post incubation 402, 406. Also, as noted above, at least time periods B, D, and E may vary from cassette to cassette, depending on the number of clinical samples that test positive for a bacterial infection.

Figure 6:
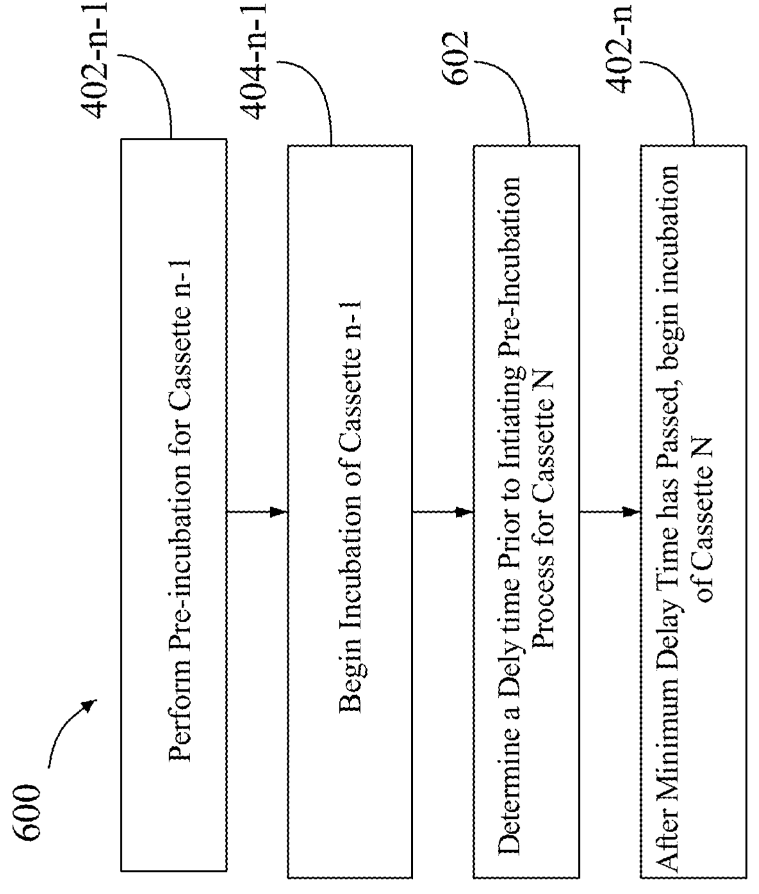
FIG. 6 is a flow chart illustrating a method of performing a sequential automated flow cytometry process on a plurality of multi-well cassettes.

FIG. 6 illustrates a method of sequentially performing the automated flow cytometry process of FIG. 4 on two multi-well cassettes. As shown in FIG. 6, at step 402-*n*-1 the pre-incubation process steps 402 (FIG. 4) are performed on a first cassette n-1. At step 404-*n*-1, the incubation of first cassette n-1 begins, and at step 602, a delay time prior to initiating the pre-incubation process 402 for a subsequent cassette n is determined. At step 402-*n*, after the required delay time after incubation of cassette n-1 has passed, the pre-incubation process 402-*n* for cassette n begins. Processor 234 may be configured to execute one or more calculations in connection with performing step 602 of FIG. 6—determination of a delay time, as well as other delay times as described below. In one example, calculations for determining a delay in a start time for analysis of a given multi-well cassette, n, may involve one or more of Equations (1)-(6) as follows:

$$t_{delay\ n} > t_{post\text{-}incubation,n\text{-}1} - t_{pre\text{-}incubation,n} \quad \text{Eq. (1)}$$

wherein: $t_{delay\ n}$ is the minimum required time delay prior to beginning a first step, e.g., step 408 of an automated flow cytometry process of a cassette, n, after an incubation period of a previously-analyzed cassette, n-1, begins;

$t_{post\text{-}incubation,\ n\text{-}}1$ is the amount of time required to complete post incubation processes, e.g., steps 422-428, after an incubation, e.g., step 404 of previously analyzed cassette, n-1; and $t_{pre\text{-}incubation,n}$ is the amount of time required to complete pre-incubation processes, e.g., steps 408-420.

$$t_{post\text{-}incubation,n\text{-}1}(x,y) = t_{D,n\text{-}1}(x) + t_{E,n\text{-}1}(y) \quad \text{Eq. (2)}$$

wherein: $t_{D,n\text{-}1}(x)$ is the amount of time required to perform a growth ratio determination process, e.g., steps 422-426; and $t_{E,n\text{-}1}(y)$ is the amount of time required to perform a bacteria susceptibility determination process, e.g., step 428.

$$t_{D,n\text{-}1}(x) = j + k * x \quad \text{Eq. (3)}$$

wherein: j is a constant, in some examples, about 5 to 15 minutes, and in some examples, about 12 minutes;

k is a constant, in some examples, about 1 to 3 minutes, and in some examples about 1.25 minutes; and x is the number of clinical samples containing a concentration of live bacteria above a threshold value, determined during a pre-incubation live bacteria enumeration process, e.g., step 316.

$$t_{E,n\text{-}1}(y) = l + m * y \quad \text{Eq. (4)}$$

wherein: l is a constant, in some examples, about 5 to 10 minutes, and in some examples, about 8 minutes; m is a constant, in some examples, about 5 to 10 minutes, and in some examples about 7 minutes; and y is the number of clinical samples containing bacteria population(s) having a rate of bacteria population expansion during an incubation period that exceeds a threshold value, determined during a post-incubation live bacteria enumeration process and comparison to a pre-incubation bacteria enumeration, e.g., step 426.

$$t_{pre\text{-}incubation,n}(c,x) = t_{A,n}(c) + t_{B,n}(x) \quad \text{Eq. (5)}$$

wherein: $t_{A,n}(c)$ is the amount of time required to perform a pre-incubation process through an initial live bacteria enumeration, e.g., steps 408-416;

$t_{B,n}(x)$ is the amount of time required to perform a pre-incubation process on x clinical samples of a cassette after an initial live bacteria enumeration, e.g., steps 418-420;

c is the number of clinical samples that can be loaded on a cassette; and x is the number of clinical samples containing a concentration of live bacteria above a threshold value, determined during a pre-incubation live bacteria enumeration process, e.g., step 416.

$$t_{B,n}(x)=n+o*x \quad \text{Eq. (6)}$$

wherein: n is a constant, in some examples, about 11 to 20 minutes, and in some examples, about 35 minutes;

o is a constant, in some examples, about 13 to 30 minutes, and in some examples, about 50 minutes; and x is the number of clinical samples containing a concentration of live bacteria above a threshold value, determined during a pre-incubation live bacteria enumeration process, e.g., step 416.

Thus, as described above, the minimum required time delay before commencing pre-incubation phase 402 is a function of the duration of the pre-incubation phase for that cassette and the post-incubation phase 406 for the previously-analyzed cassette. As noted above, the time duration of the post-incubation phase is a function of the number of clinical samples contained on the cassette that tested positive in the initial screening step 416, and the number of samples that tested positive in the growth ratio calculation step 426 (FIG. 4). Thus, the minimum required time delay for cassette n increases as the number of clinical samples on cassette n-1 containing a bacterial infection increase. As will be appreciated, Equation (1) represents a minimum time delay and a longer time delay prior to commencement of analysis of a subsequent cassette may be used. Further, the example described above assumes a constant incubation time for all cassettes, however, Equations 1-6 can be readily modified to incorporate a variable incubation time, which may be applicable when cassettes with differing types of fluids, e.g., urine, blood, and/or cerebral spinal fluid, are being analyzed by system 200 at the same time. In another example, system 10 may incorporate two time delays. For example, the initial time delay $t_{delay\ n}$ may assume a nominal number of samples on cassette 300 will test positive in screening step 416. As illustrated in Equations 1, 5, and 6, if the assumption over-predicts the number of infected samples, the time duration of the pre-incubation phase will be shorter, requiring a longer minimum time delay tdelay n. A second time delay may be incorporated prior to commencing with step 418 to account for the over-prediction to ensure cassette n does not begin incubation too soon.

As will be appreciated, one or more of software modules 240 may include machine executable instructions, executable by processor 234, for automatically determining any required time delays prior to processing a multi-well cassette, which may involve accessing the results from one or more of steps 416, 424 and 426, which may be stored in memory 236 and for otherwise coordinating the parallel processing of a plurality of multi-well cassettes 300 with one or more flow cytometers 222.

Figure 7:
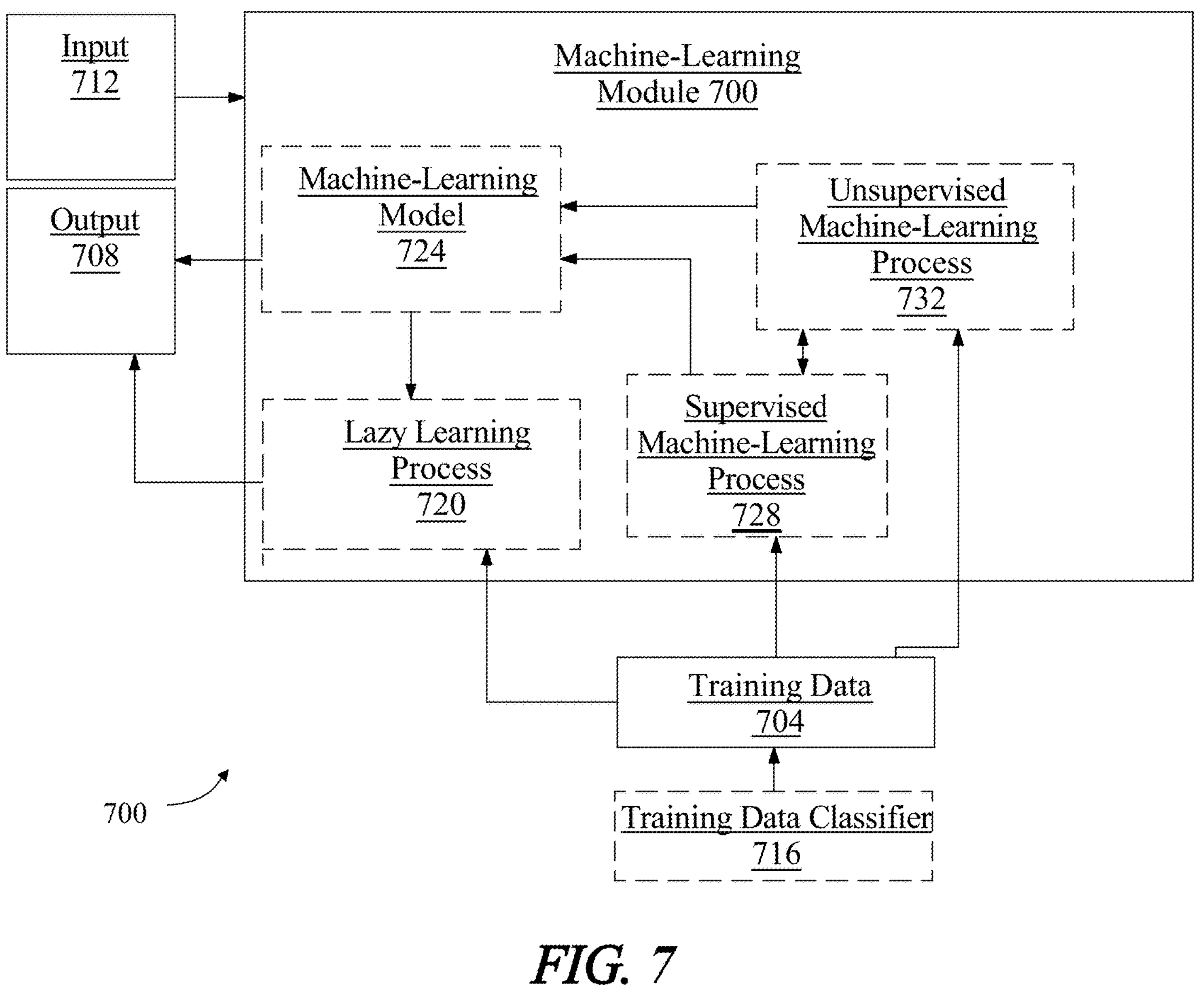
FIG. 7 is a block diagram of an exemplary machine-learning process.

Referring now to FIG. 7, an exemplary embodiment of a machine-learning module 700 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 704 to generate an algorithm that will be performed by a computing device/module to produce outputs 708 given data provided as inputs 712; this is in contrast to a non-machine learning software program where the commands to be executed are determined in advance by a user and written in a programming language.

Still referring to FIG. 7, "training data," as used herein, is data containing correlations that a machine-learning process may use to model relationships between two or more categories of data elements. For instance, and without limitation, training data 704 may include a plurality of data entries, each entry representing a set of data elements that were recorded, received, and/or generated together; data elements may be correlated by shared existence in a given data entry, by proximity in a given data entry, or the like. Multiple data entries in training data 704 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 704 according to various correlations; correlations may indicate causative and/or predictive links between categories of data elements, which may be modeled as relationships such as mathematical relationships by machine-learning processes as described in further detail below. Training data 704 may be formatted and/or organized by categories of data elements, for instance by associating data elements with one or more descriptors corresponding to categories of data elements. As a non-limiting example, training data 704 may include data entered in standardized forms by persons or processes, such that entry of a given data element in a given field in a form may be mapped to one or more descriptors of categories. Elements in training data 704 may be linked to descriptors of categories by tags, tokens, or other data elements; for instance, and without limitation, training data 704 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively, or additionally, and continuing to refer to FIG. 7, training data 704 may include one or more elements that are not categorized; that is, training data 704 may not be formatted or contain descriptors for some elements of data. Machine-learning algorithms and/or other processes may sort training data 704 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 704 to be made applicable for two or more distinct machine-learning algorithms as described in further detail below. Training data 704 used by machine-learning module 700 may correlate any input data as described in this disclosure to any output data as described in this disclosure.

Further referring to FIG. 7, training data may be filtered, sorted, and/or selected using one or more supervised and/or unsupervised machine-learning processes and/or models as described in further detail below; such models may include without limitation a training data classifier 716. Training data classifier 716 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 700 may generate a classifier using a classification algorithm, defined as a processes whereby a computing device and/or any module and/or component operating thereon derives a classifier from training data 704. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 7, machine-learning module 700 may be configured to perform a lazy-learning process 720 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 704. Heuristic may include selecting some number of highest-ranking associations and/or training data 704 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 7, machine-learning processes as described in this disclosure may be used to generate machine-learning models 724. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 724 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 724 may be generated by creating an artificial neural network, such as a convolutional neural network comprising an input layer of nodes, one or more intermediate layers, and an output layer of nodes. Connections between nodes may be created via the process of "training" the network, in which elements from a training data 704 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 7, machine-learning algorithms may include at least a supervised machine-learning process 728. At least a supervised machine-learning process 728, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a first enumeration of total bacteria or a second enumeration of total bacteria as described above as inputs, autonomous functions as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 704. Persons skilled in the art, upon reviewing the entirety of this disclosure, will be aware of various possible variations of at least a supervised machine-learning process 728 that may be used to determine relation between inputs and outputs. Supervised machine-learning processes may include classification algorithms as defined above.

Further referring to FIG. 7, machine learning processes may include at least an unsupervised machine-learning processes 732. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 7, machine-learning module 700 may be designed and configured to create a machine-learning model 724 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 7, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

For example, and still referring to FIG. 7, neural network also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 7, a node may include, without limitation a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function $\varphi$, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above. In an embodiment, and without limitation, a neural network may receive semantic units as inputs and output vectors representing such semantic units according to weights $w_i$ that are derived using machine-learning processes as described in this disclosure.

Figure 8:
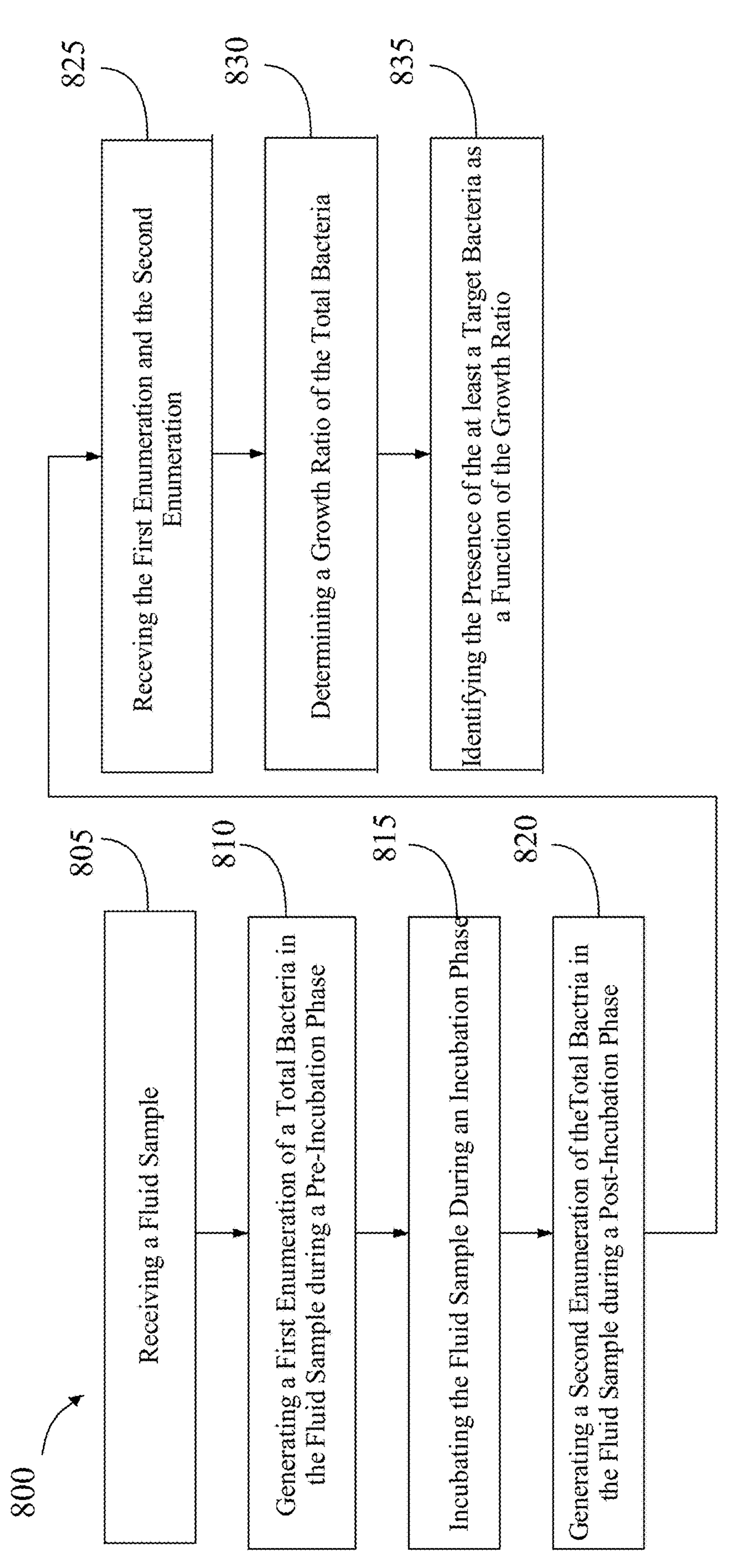
FIG. 8 is a flow chart illustrating a method for detecting a target bacteria.

Referring to FIG. 8, an exemplary method 800 for method for detecting a target bacteria is shown. Method 800 includes a step 805 of receiving, at a flow cytometer, a fluid sample, wherein the fluid sample comprises at least a target bacteria population and at least a contaminant bacteria population. This may be implemented in accordance with FIGS. 1-7. In some embodiments, the at least a contaminant bacteria may comprise all bacteria within the fluid sample that is not the target bacteria. In other embodiments, the target bacteria may include pathogenic bacteria. The fluid sample may be contained within multi-well cassettes. In other embodiments, the flow cytometer may comprise at least a fluid handling system. The fluid samples may include urine, blood, or cerebral spinal fluid.

With continued reference to FIG. 8, method 800 includes a step 810 of generating, at the flow cytometer, a first enumeration of a total bacteria in the fluid sample during a pre-incubation phase, wherein total bacteria comprises an aggregate of the at least a target bacteria and the at least a contaminant bacteria. This may be implemented in accordance with FIGS. 1-7. In some embodiments, the pre-incubation phase may include adjusting the fluid sample concentration by way of dilution or adding a growth media. In other embodiments, the flow cytometer is configured to differentiate between the target bacteria and the at least a contaminant bacteria using staining techniques.

With continued reference to FIG. 8, method 800 includes a step 815 of incubating, at the flow cytometer, the fluid sample during an incubation phase. This may be implemented in accordance with FIGS. 1-7. In some embodiment, the fluid sample may be incubated as a function of an incubation parameter.

With continued reference to FIG. 8, method 800 includes a step 820 of generating, at the flow cytometer, a second enumeration of the total bacteria in the fluid sample during a post-incubation phase. This may be implemented in accordance with FIGS. 1-7.

With continued reference to FIG. 8, method 800 includes a step 825 of receiving, at a computing device, the first enumeration and the second enumeration. This may be implemented in accordance with FIGS. 1-7.

With continued reference to FIG. 8, method 800 includes a step 830 of determining, at the computing device, a growth ratio of the total bacteria as a function of the first enumeration and the second enumeration. This may be implemented in accordance with FIGS. 1-7. In some embodiments, the method may further include determining, at the computing device, a diagnosis as a function of the growth ratio and one or more of the first enumeration and the second enumeration.

With continued reference to FIG. 8, method 800 includes a step 835 of identifying, at the computing device, the presence of the at least a target bacteria as a function of the growth ratio. This may be implemented in accordance with FIGS. 1-7.

Any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
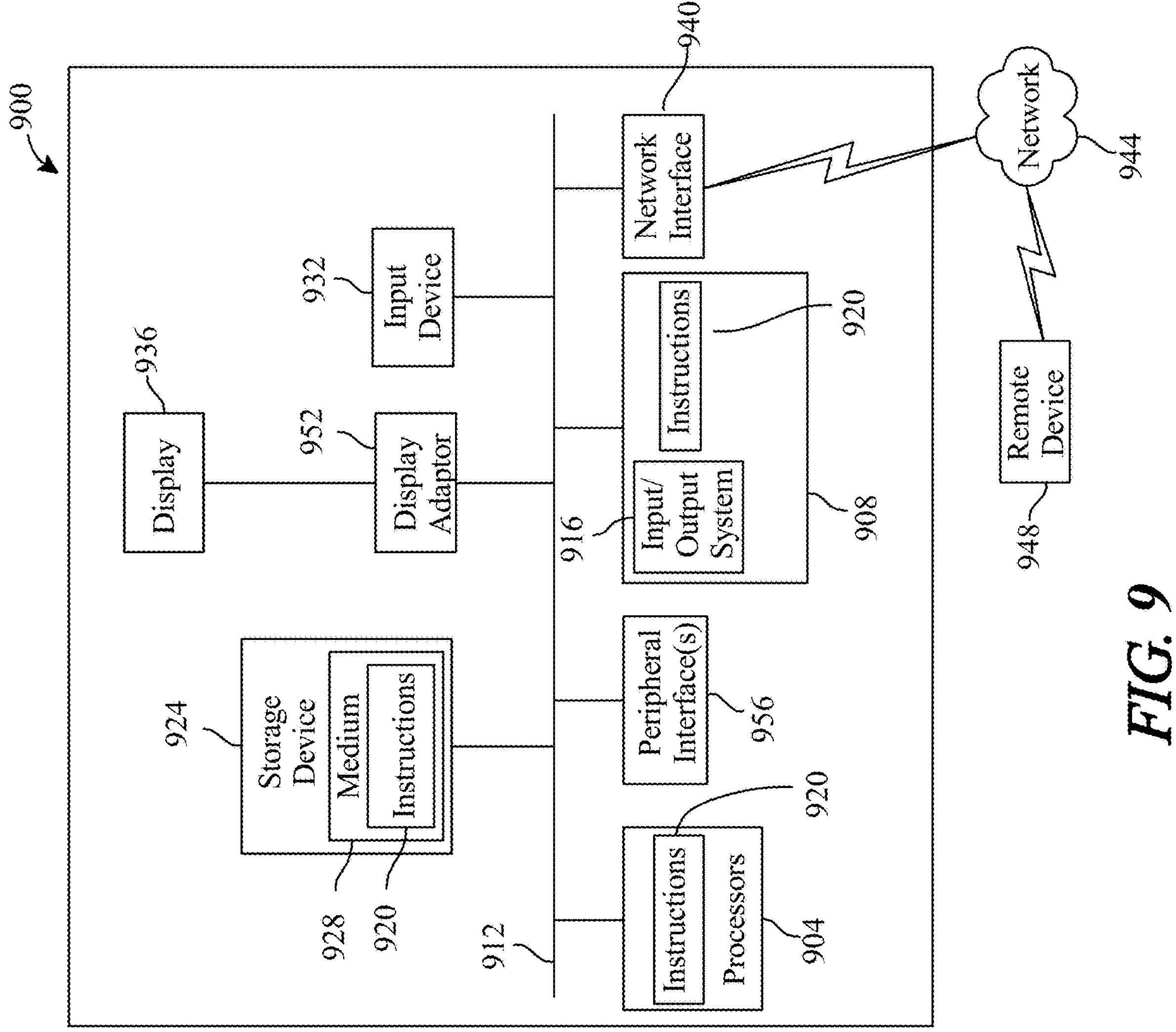
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system, such as the automated flow cytometry system of FIG. 1, to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIRE-WIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. It is noted that in the present specification and claims appended hereto, conjunctive language such as is used in the phrases "at least one of X, Y and Z" and "one or more of X, Y, and Z," unless specifically stated or indicated otherwise, shall be taken to mean that each item in the conjunctive list can be present in any number exclusive of every other item in the list or in any number in combination with any or all other item(s) in the conjunctive list, each of which may also be present in any number. Applying this general rule, the conjunctive phrases in the foregoing examples in which the conjunctive list consists of X, Y, and Z shall each encompass: one or more of X; one or more of Y; one or more of Z; one or more of X and one or more of Y; one or more of Y and one or more of Z; one or more of X and one or more of Z; and one or more of X, one or more of Y and one or more of Z.

Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for detecting at least a target bacteria, wherein the system comprises:

a flow cytometer configured to:

receive a fluid sample comprising the at least a target bacteria and at least a contaminant bacteria;

generate a first enumeration of a total bacteria in the fluid sample during a pre-incubation phase, wherein the total bacteria comprises an aggregate of the at least a target bacteria and the at least a contaminant bacteria;

generate a second enumeration of the total bacteria in the fluid sample during a post-incubation phase;

an incubator configured to incubate the fluid sample during an incubation phase as a function of a plurality of incubation parameters, the plurality of incubation parameters including at least an incubation temperature and an agitation parameter, wherein the plurality of incubation parameters are selected from a lookup table that relates the plurality of incubation parameters to the target bacteria;

an automated cassette handling device comprising one or more robotic components controlled by a processor, wherein the automated cassette handling device is configured to automatedly transport the fluid sample between the incubator and the flow cytometer for analysis by the flow cytometer;

a machine-learning module executed by the processor, wherein the machine-learning module is configured to:

determine a delay time as a function of a duration of the pre-incubation phase of a current cassette and a duration of a post-incubation phase of a previously analyzed cassette, wherein the duration of the post-incubation phase is dependent on results of analysis of the previously analyzed cassette; and determine a second delay time configured to prevent premature incubation by accounting for over-prediction of the post-incubation phase duration;

wherein the automated cassette handling device is configured to transport the fluid sample between the incubator and the flow cytometer in accordance with the delay time and the second delay time; and a computing device, wherein the computing device is configured to:

utilize a flow cytometer software module to access pre-defined regions of interest, scatter values and fluorescence values which are stored in a fluid library for detecting various species of bacteria in various fluids being tested, wherein detections of pre-defined regions of interests possessing characteristics of target events comprising at least scatter values, as determined by a computational analysis executed by the flow cytometer software, are used to determine a concentration of particles for a bacteria count, wherein the bacteria count excludes dead bacteria;

generate the plurality of incubation parameters based on a type of the at least a target bacteria and a type of the fluid sample;

receive the first enumeration and the second enumeration;

determine a growth ratio of the total bacteria as a function of the first enumeration and the second enumeration;

identify a presence of the at least a target bacteria as a function of the growth ratio and information gathered from the flow cytometer software module; and determine a diagnosis as a function of the growth ratio and one or more of the first enumeration and the second enumeration, wherein determining the diagnosis comprises implementing a lookup table to perform an array indexing operation.

2. The system of claim 1, wherein the at least a contaminant bacteria comprises all bacteria within the fluid sample that is not the target bacteria.

3. The system of claim 1, wherein the at least a target bacteria comprises a pathogenic bacteria.

4. The system of claim 1, wherein the fluid sample is contained within multi-well cassettes.

5. The system of claim 1, wherein the pre-incubation phase additionally comprises adjusting a concentration of the fluid sample by diluting the fluid sample.

6. The system of claim 1, wherein the flow cytometer is further configured to differentiate the target bacteria and the at least a contaminant bacteria using staining techniques.

7. The system of claim 1, wherein the pre-incubation phase additionally comprises adjusting a concentration of the fluid sample by way of adding a growth media.

8. The system of claim 1, wherein the fluid sample comprises urine.

* * * * *